(12) United States Patent
Clare et al.

(10) Patent No.: US 10,107,736 B2
(45) Date of Patent: Oct. 23, 2018

(54) HYDROGEL COMPOSITIONS AND METHODS FOR ELECTROCHEMICAL SENSING

(71) Applicant: Portland State University, Portland, OR (US)

(72) Inventors: Tami Lasseter Clare, Portland, OR (US); Alice H. England, Portland, OR (US)

(73) Assignee: Portland State University, Portland, OR (US)

( * ) Notice: Subject to any disclaimer, the term of this patent is extended or adjusted under 35 U.S.C. 154(b) by 198 days.

(21) Appl. No.: 14/896,509

(22) PCT Filed: Jun. 10, 2014

(86) PCT No.: PCT/US2014/041743
§ 371 (c)(1),
(2) Date: Dec. 7, 2015

(87) PCT Pub. No.: WO2014/201023
PCT Pub. Date: Dec. 18, 2014

(65) Prior Publication Data
US 2016/0123865 A1      May 5, 2016

Related U.S. Application Data

(60) Provisional application No. 61/833,438, filed on Jun. 10, 2013.

(51) Int. Cl.
*G01F 1/64* (2006.01)
*G01N 17/00* (2006.01)
(Continued)

(52) U.S. Cl.
CPC ........... *G01N 17/02* (2013.01); *C08F 265/02* (2013.01); *C08L 33/26* (2013.01); *C09J 133/26* (2013.01); *G01N 27/30* (2013.01)

(58) Field of Classification Search
None
See application file for complete search history.

(56) References Cited

U.S. PATENT DOCUMENTS 5,441,772 A * 8/1995 McAndrew .............. B05D 7/16
427/386
6,313,646 B1 * 11/2001 Davis ..................... G01N 17/02
204/404

(Continued)

FOREIGN PATENT DOCUMENTS

CA       1 181 582       1/1985
JP       2006/249258 A   9/2006
(Continued)

OTHER PUBLICATIONS

Cano et al., "Use of EIS for the evaluation of the protective properties of coatings for metallic cultural heritage: a review," published in *J. Solid State Electrochemistry*, online prepublication provided (Aug. 11, 2009; 29 pages), final publication in vol. 14, No. 3, pp. 381-391, 2010.

(Continued)

*Primary Examiner* — Eli S Mekhlin
(74) *Attorney, Agent, or Firm* — Klarquist Sparkman, LLP

(57) ABSTRACT

Embodiments of hydrogels for electrochemical sensing, electrodes comprising the hydrogels, and methods of making and using the hydrogels are disclosed. The disclosed hydrogel electrodes comprise a cross-linked poly(acrylic acid-co-2-acrylamido-2-methyl-1-propanesulfonic acid (poly(AA-AMPS)) hydrogel and an electrical contact.

18 Claims, 6 Drawing Sheets

(51) Int. Cl.
  *G01N 27/26*  (2006.01)
  *G01N 17/02*  (2006.01)
  *C09J 133/26*  (2006.01)
  *C08L 33/26*  (2006.01)
  *G01N 27/30*  (2006.01)
  *C08F 265/02*  (2006.01)

(56) References Cited

U.S. PATENT DOCUMENTS

| 2004/0087671 | A1* | 5/2004 | Tamada | A61B 5/1486 |
| | | | | 516/99 |
| 2009/0005667 | A1* | 1/2009 | Cui | A61B 5/04087 |
| | | | | 600/395 |

FOREIGN PATENT DOCUMENTS

| JP | 2009/227924 A | 10/2009 |
| JP | 2012/153884 A | 8/2012 |

OTHER PUBLICATIONS

Cano et al., "Electrochemical characterization of organic coatings for protection of historic steel artifacts," *J. Solid State Electrochemistry*, online prepublication provided (Aug. 11, 2009; 18 pages), final publication in vol. 14, No. 3, pp. 453-463, 2010.

Cano et al., "A novel gel polymer electrolyte cell for in-situ application of corrosion electrochemical techniques," *Electrochemistry Communications*, vol. 41, pp. 16-19, online publication Jan. 23, 2014.

Clare et al., "Evaluation of fluorinated protective coatings for outdoor metals," *Proceed. of the ICOM-CC Metal 07 WG, Protection of Metal Artifacts*, vol. 5, pp. 83-87, 2007.

Corbellini et al., "Noninvasive solution for electrochemical impedance spectroscopy on metallic works of art," *IEEE Transactions on Instrumentation and Measurement*, vol. 61, No. 5, pp. 1193-1200, May 5, 2012.

Degrigny, "Use of electrochemical techniques for the conservation of metal artefacts: a review," *J. Solid State Electrochemistry*, vol. 14, No. 3, pp. 353-361, 2010.

England et al., "Synthesis and Characterization of Flexible Hydrogel Electrodes for Electrochemical Impedance Measurements of Protective Coatings on Metal Sculptures," *Electroanalysis*, vol. 26, pp. 1059-1067, 2014.

International Search Report and Written Opinion for corresponding PCT Application No. PCT/US2014/041743, dated Aug. 13, 2014.

Kosec et al., "The comparison of organic protective layers on bronze and copper," *Progress in Organic Coatings*, vol. 69, No. 2, pp. 199-206, 2010.

Qi et al., "Two-Electrode Electrochemical Impedance Sensor: Part 1-Response to Coating Degradation on Conductive Substrates," *Corrosion*, vol. 65, No. 5, pp. 343-349, 2009.

Qi et al., "Two-Electrode Electrochemical Impedance Sensor: Part 2-Impedance Measurement and Simulation of Coatings on Non-metal Subtrates," *Corrosion*, vol. 66, No. 2, Article 025002, 10 pp., 2010.

Swartz et al., "Understanding the differences in film formation mechanisms of two comparable solvent based and water-borne coatings on bronze substrates by electrochemical impedance spectroscopy," *Electrochimica Acta*, prepublication copy provided, final publication in vol. 62, pp. 199-206, 2012.

Swartz et al. "Characterizing and improving performance properties of thin solid films produced by weatherable water-borne colloidal suspensions on bronze substrates," *Progress in Organic Coatings*, vol. 75, No. 3, pp. 215-223, 2012.

Carullo, et al., "Low-Cost Electrochemical Impedance Spectroscopy System for Corrosion Monitoring of Metallic Antiquities and Works of Art," *IEEE Transactions on Instrumentation and Measurement*, vol. 49, No. 2, Apr. 2000, pp. 371-375.

Eggins, Brian R., "Skin Contact Electrodes for Medical Applications," *Analyst*, 118, Apr. 1993, pp. 439-442. vol.

Extended European Search Report, dated Nov. 8, 2016, issued in corresponding European Patent Application No. 14810867.3, 10 pp.

* cited by examiner

HYDROGEL COMPOSITIONS AND METHODS FOR ELECTROCHEMICAL SENSING

CROSS REFERENCE TO RELATED APPLICATIONS

This application is the U.S. National Stage of International Application No. PCT/US2014/041743, filed Jun. 10, 2014, which was published in English under PCT Article 21(2), which in turn claims the benefit of U.S. Provisional Application No. 61/833,438, filed Jun. 10, 2013, each of which is incorporated by reference in its entirety.

ACKNOWLEDGMENT OF GOVERNMENT SUPPORT

This invention was made with government support under grant No. 1139230 awarded by the National Science Foundation. The government has certain rights in the invention.

FIELD

This disclosure concerns embodiments of hydrogels, electrodes comprising the hydrogels, and methods of making and using the hydrogels.

BACKGROUND

Corrosion of artistic and historic metalwork is the primary means for their deterioration, while developing methods to better protect these works and monitor the efficacy of protective treatments remain central research questions (Degrigny, *J. Solid State Electrochemistry* 14, 3:353-361, 2010; Cano, et al., *J. Solid State Electrochemistry* 14, 3:381-391, 2010; Clare, et al., *Proceed. of the ICOM-CC Metal 07 WG, Protection of Metal Artifacts*, 83-87, 2007). To prevent degradation and corrosion of outdoor artwork, pigmented or clear protective coatings must be applied periodically because of the effects of pollutants, salts, light and moisture. Monitoring methods must be non-invasive so as to not damage or alter the substrate, and they must measure a relevant parameter. Coating gloss, thickness and/or wettability are commonly reported parameters used to monitor changes induced by weathering over time. Collections care personnel rely on visible changes (e.g. chalking, flaking and corrosion) to determine when coating reapplication is needed. However, these changes are cues of coating failure and signal that non-reversible damage to the underlying artwork has already occurred. While changes in the visual appearance of coatings are important, they may not directly correlate with changes in the permeability or porosity of a coating. It is conceivable that a coating may thin and lose gloss while remaining protective or become porous to electrolytes while maintaining film thickness.

Both electrochemical measurements and corrosion processes rely on the movement of electrons; thus electrochemical monitoring is perfectly suited to detect corrosion. There is a need to monitor the performance of coatings in situ to 1) verify that freshly applied coatings have acceptable barrier properties and are continuous, and 2) to ensure that weathered coatings have remained protective.

Electrochemical Impedance Spectroscopy (EIS) can be used to detect changes in the barrier properties of weathering coatings because it is fast, non-destructive, and being a frequency-based measurement, gives insight into the time constants of various surface-layer processes. Despite these advantages, three significant hurdles have prevented widespread use of EIS by the conservation community: 1) electrochemical testing typically requires artwork to be conductive and wired directly to instrumentation at an uncoated region of the artwork; 2) field-deployable equipment for these measurements is not available; and 3) rigid fluid-filled chambers are incompatible with the contoured surfaces of most outdoor metalwork.

SUMMARY

Embodiments of hydrogel compositions, electrodes comprising a hydrogel composition, and methods of making and using the same are disclosed. Embodiments of a hydrogel electrode include (i) a cross-linked poly(acrylic acid-co-2-acrylamido-2-methyl-1-propanesulfonic acid (poly(AA-AMPS)) hydrogel comprising 2-acrylamido-2-methyl-1-propanesulfonic acid and poly(acrylic acid), wherein the hydrogel has an impedance of less than 10 k$\Omega$ at 0.1 Hz; and (ii) an electrical contact in contact with the hydrogel. The electrical contact may be a metal foil or a metal mesh.

In some embodiments, the cross-linked hydrogel comprises 17-25 wt % 2-acrylamido-2-methyl-1-propanesulfonic acid and 10-20 wt % poly(acrylic acid) and/or has a weight percent ratio of 2-acrylamido-2-methyl-1-propanesulfonic acid to poly(acrylic acid) from 1.5 to 2.0. Suitable cross-linkers include N,N'-methylenebis(acrylamide). The cross-linked hydrogel may include 50-65 wt % water. In some embodiments, the cross-linked hydrogel further comprises a humectant, such as glycerol. The cross-linked hydrogel may further comprise an ionic electrolyte. In certain embodiments, the cross-linked hydrogel has a swellability, $q_r \leq 1000\%$.

Embodiments of the disclosed electrodes are suitable for evaluating permeability of a coating on a substrate. The substrate may be planar or non-planar. In one embodiment, a method for evaluating permeability includes (i) placing a first hydrogel electrode in contact with the coating, (ii) placing a second hydrogel electrode in contact with the coating and laterally spaced apart from the first electrode, (iii) applying an alternating current between the first electrode and the second electrode, (iv) recording an electrochemical impedance spectrum, and (v) evaluating the electrochemical impedance spectrum to determine whether the coating is permeable to ions.

In another embodiment, a method for evaluating permeability of a coating on a surface of an electrically conductive substrate includes (i) placing a first hydrogel electrode in contact with the coating, (ii) applying an alternating current between the first electrode and an opposing surface of the electrically conductive substrate, (iii) recording an electrochemical impedance spectrum, and (iv) evaluating the electrochemical impedance spectrum to determine whether the coating is permeable to ions.

When the coating is a polymer- or wax-based coating, a total impedance >1 M$\Omega$ in a frequency range less than 1 Hz may indicate that the coating is non-permeable to ions. When the coating is a corrosion inhibitor coating, a total impedance >10 k$\Omega$ in a frequency range less than 1 Hz may indicate that the coating is non-permeable to ions.

In one embodiment, the method further includes determining whether the electrochemical impedance spectrum deviates from linearity over a measured frequency range, wherein nonlinearity indicates the coating is permeable to ions. In another embodiment, the method further includes determining a time constant, wherein a time constant of less than 75 milliseconds indicates the coating is non-permeable to ions.

The disclosure also encompasses kits for evaluating permeability of a coating on a substrate. Embodiments of a kit include a hydrogel or a hydrogel electrode as disclosed herein. The kit further may include an electrolyte solution.

The foregoing and other objects, features, and advantages of the invention will become more apparent from the following detailed description, which proceeds with reference to the accompanying figures.

DETAILED DESCRIPTION

I. Terms and Definitions

Figure 1:
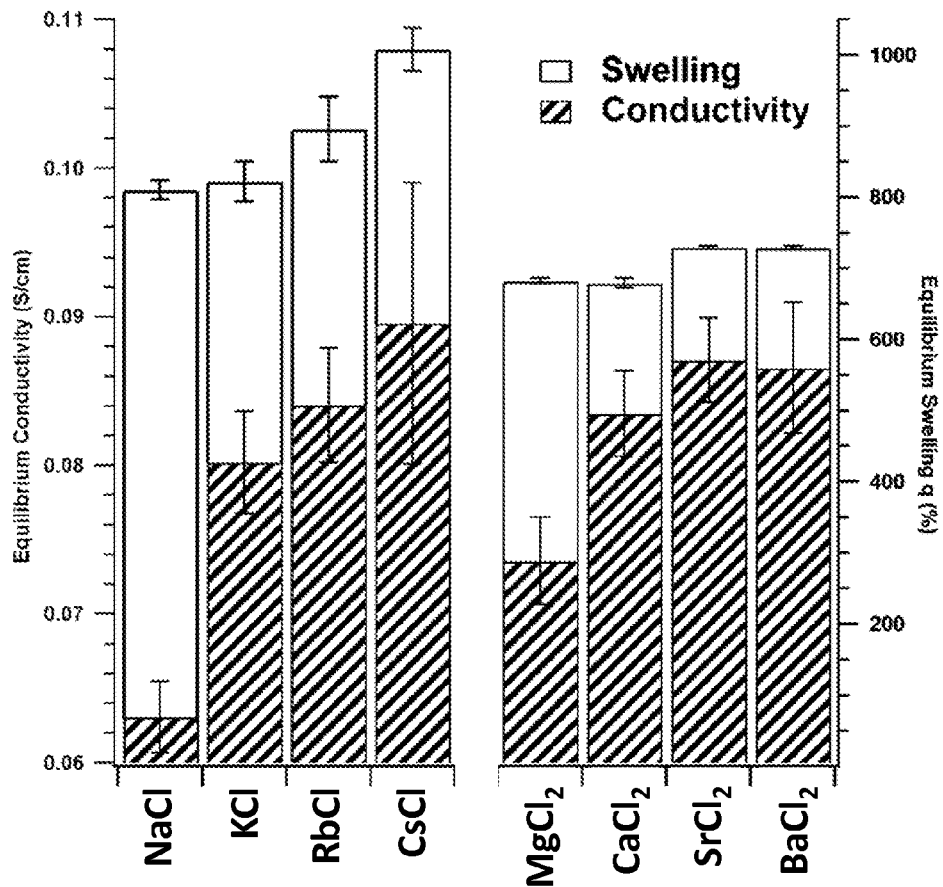
FIG. 1 is a graph showing the relationship between swelling and conductivity for hydrogels soaked in various electrolytes.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

AMPS: 2-Acrylamido-2-methyl-1-propanesulfonic acid.

Corrosion: Electrochemical oxidation of metals in contact with an oxidant, e.g., oxygen. Typically metal oxides and/or metal salts are formed.

EIS: Electrochemical impedance spectrum.

Electrolyte: A substance containing free ions that behaves as an electrically conductive medium. Electrolytes generally comprise ions in a solution, but molten electrolytes and solid electrolytes also are known.

Flash rust: Flash rusting can occur when a thin film of water is present on the metal surface and/or when small metal particles become moistened. Flash rusting can occur during surface preparation. In contrast to long-term corrosion, flash-rusting may occur in a matter of hours. A flash rust inhibitor may be added to a water-based coating to stop corrosion that occurs during the drying process. Flash rusting can quickly bleed through and stain the coating.

Humectant: A hygroscopic substance that attracts and retains moisture via absorption. Humectants often are molecules including several hydrophilic groups, e.g., hydroxyl groups, amines, or carboxyl groups. Exemplary humectants include, but are not limited to, propylene glycol, hexylene glycol, butylene glycol, glyceryl triacetate, vinyl alcohol, sugar alcohols (e.g., glycerol, sorbitol, xylitol), polymeric polyols, urea, and alpha hydroxy acids.

Hydrogel: A substance formed when a hydrophilic organic polymer (natural or synthetic) is cross-linked via covalent, ionic, and/or hydrogen bonds to create a three-dimensional open-lattice structure which takes up water molecules to form a gel. When a hydrogel takes up soluble electrolytes, it may become conductive.

Impedance: Electrical impedance measures the opposition in an electrical circuit to passage of current when a voltage is applied. When direct current is applied to a circuit, impedance is the same as resistance. However, when alternating current is applied, impedance has both magnitude (resistance) and phase. The magnitude is the ratio of the voltage amplitude to the current amplitude, and the phase is the phase shift by which the current is ahead of the voltage. Impedance typically is measured in ohms.

MBA: N,N'-methylenebis(acrylamide).

PAA: Poly(acrylic acid).

Permeable: Permeable means capable of being passed through. The term permeable is used especially for materials through which gases or liquids may pass. Permeability is the quality or state of being permeable.

Polymer: A molecule of repeating structural units (e.g., monomers) formed via a chemical reaction, i.e., polymerization.

Substrate: A substance or layer that underlies something. As used herein, the term substrate refers to the surface or object on which a coating is applied.

Time constant: As used herein, the term "time constant" refers to the inverse of the frequency when the phase angle, θ, is equal to −45°

Wax: An organic compound including long alkyl chains. Waxes may be esters of carboxylic acids, long chain alcohols, and/or substituted or unsubstituted hydrocarbons (e.g., n- and iso-alkanes, naphthenes, alkyl-substituted aromatic compounds, and naphthene-substituted aromatic compounds). Waxes are solids at ambient temperature, and become liquid when heated.

II. Overview of Various Embodiments

Embodiments of an electrode comprise a cross-linked poly(acrylic acid-co-2-acrylamido-2-methyl-1-propanesulfonic acid (poly(AA-AMPS)) hydrogel comprising 2-acrylamido-2-methyl-1-propanesulfonic acid and poly(acrylic acid), wherein the hydrogel has an impedance of less than 10 kΩ at 0.1 Hz; and an electrical contact in contact with the hydrogel. The cross-linked poly(AA-AMPS) hydrogel may comprise 17-25 wt % 2-acrylamido-2-methyl-1-propanesulfonic acid and 10-20 wt % poly(acrylic acid). In some embodiments, the cross-linked poly(AA-AMPS) hydrogel has a weight percent ratio of 2-acrylamido-2-methyl-1-propanesulfonic acid to poly(acrylic acid) from 1.5 to 2.0.

In any or all of the above embodiments, the cross-linked poly(AA-AMPS) hydrogel may comprise 50-65 wt % water. In any or all of the above embodiments, the cross-linked poly(AA-AMPS) hydrogel may comprise 0.2-0.3 wt % N,N'-methylene-bis(acrylamide).

In any or all of the above embodiments, the cross-linked poly(AA-AMPS) hydrogel may further comprise a humectant. In some embodiments, the humectant is glycerol, and the cross-linked poly(AA-AMPS) hydrogel comprises 7-18 wt % glycerol.

In any or all of the above embodiments, the electrode may further comprise an ionic electrolyte. In some embodiments, the ionic electrolyte comprises NaCl, KCl, RbCl, CsCl, $MgCl_2$, $CaCl_2$, $SrCl_2$, $BaCl_2$, $K_2SO_4$, 2-[4-(2-hydroxyethyl)-piperazin-1-yl]ethanesulfonic acid potassium salt, piperazine-1,4-bis-2-ethanesulfonic acid potassium salt, $KHCO_3$, $K_2CO_3$, $KC_2H_3O_2$, KBr, KI, $K_3PO_4$, $KH_2PO_4$, $K_2HPO_4$), $Na_2SO_3$, 2-[4-(2-hydroxyethyl)piperazin-1-yl]ethanesulfonic acid sodium salt, piperazine-1,4-bis-2-ethanesulfonic acid sodium salt, $Ca(C_2H_3O_2)_2$, $Ca(NO_3)_2$, or a combination thereof.

In any or all of the above embodiments, the cross-linked hydrogel may have a maximum gel swelling, $q_t$, ≤1000%.

In any or all of the above embodiments, the electrical contact may be a metal foil or mesh. In some embodiments, the metal foil or mesh is a silver, gold, nickel, or platinum foil or mesh.

One independent embodiment of a method for evaluating permeability of a coating on a substrate comprises placing a first electrode as disclosed herein in contact with the coating; placing a second electrode as disclosed herein in contact with the coating and laterally spaced apart from the first electrode; applying an alternating current between the first electrode and the second electrode; recording an electrochemical impedance spectrum; and evaluating the electrochemical impedance spectrum to determine whether the coating is permeable to ions. In some embodiments, the first electrode and the second electrode have the same chemical composition. In any or all of the above embodiments, the substrate may not be electrically conductive.

One independent embodiment of a method evaluating permeability of a coating on a surface of an electrically conductive substrate comprises placing a first electrode as disclosed herein in contact with the coating; applying an alternating current between the first electrode and an opposing surface of the electrically conductive substrate; recording an electrochemical impedance spectrum; and evaluating the electrochemical impedance spectrum to determine whether the coating is permeable to ions.

In any or all embodiments of the above methods, the alternating current may be 5-40 $mV_{rms}$. In any or all embodiments of the above methods, the substrate may be nonplanar.

In some embodiments of the above methods, the coating is a polymer- or wax-based coating, and a total impedance >1 MΩ in a frequency range less than 1 Hz indicates the coating is non-permeable to ions. In some embodiments of the above methods, the coating is a corrosion inhibitor coating, and a total impedance >10 kΩ in a frequency range less than 1 Hz indicates the coating is non-permeable to ions.

In any or all embodiments of the above methods, the electrochemical impedance spectrum may be measured over a range from 0.1 Hz to 1,000 Hz, and the method further comprises determining whether the electrochemical impedance spectrum deviates from linearity over a measured frequency range, wherein nonlinearity indicates the coating is permeable to ions. In any or all embodiments of the above methods, the method may further include determining a time constant, wherein a time constant of less than 75 milliseconds indicates the coating is non-permeable to ions.

This disclosure also includes embodiments of a kit comprising an electrode as disclosed herein. In some embodiments, the kit further comprises an electrolyte solution.

III. Hydrogels

Embodiments of flexible hydrogels comprising cross-linked poly(acrylic acid-co-2-acrylamido-2-methyl-1-propanesulfonic acid) (poly(AA-AMPS)) are disclosed. In some embodiments, the weight percent ratio of 2-acrylamido-2-methyl-1-propanesulfonic acid (AMPS) to poly(acrylic acid) (PAA) in the gel ranges from 1.5 to 2.0, such as from 1.5 to 1.8, or from 1.6 to 1.8. In some examples, the ratio was 1.6-1.7. The final composition of the hydrogel comprises 15-25 wt % AMPS, such as 17-25 wt % AMPS or 15-20 wt % AMPS, and 10-20 wt % PAA, such as 10-15 wt % PAA. For example, the hydrogel may comprise 17-20 wt % AMPS and 10-12 wt % PAA.

Embodiments of the hydrogel further comprise a cross-linker, water, and trace amounts of polymerization initiators. Any cross-linker capable of cross-linking p(AA-AMPS) can be used. One exemplary cross-linker is N,N'-methylenebis(acrylamide) (MBA). In some embodiments, the cross-linker is added in an amount equal to 1-2 wt % of the mass of AMPS, such as 1-1.5 wt % of the mass of Amps, or 1.2 wt % of the mass of AMPS. In a working embodiment, the hydrogel included 18-19 wt % AMPS and 0.2-0.3 wt % MBA.

Suitable polymerization initiators include, but are not limited to, potassium persulfate, potassium metabisulfite, and iron (II) sulfate. Trace amounts (e.g., less than 0.1 wt %) of the initiator(s) may be present in the hydrogel. In some embodiments, the initiator(s) is added in an amount equal to 0.05-0.15 wt % of the mass of AMPS. In one embodiment, potassium persulfate and potassium metabisulfite were added in amounts equal to 0.075-0.15 wt % of AMPS, such as 0.1 wt %. In another embodiment, iron (II) sulfate was added in an amount equal to 0.05-0.075 wt % of AMPS.

The hydrogel also may include a humectant. Suitable humectants include sugar polyols, e.g., glycerol, sorbitol, xylitol. In some embodiments, the hydrogel comprises 7-18 wt % humectant, such as from 9-13 wt % glycerol.

The hydrogel further comprises water. In some embodiments, the hydrogel comprises 50-65 wt % water. The amount of water absorbed by the hydrogel may depend, in part, on the extent of cross-linking within the polymer matrix. As the percentage of water in the hydrogel increases, the hydrogel becomes more mechanically fragile and may tear easily.

To provide conductivity, the hydrogel is soaked in an electrolyte. An electrolyte is incorporated into the hydrogel by soaking the polymerized gel in an electrolyte solution. Suitable electrolytes include, but are not limited to, chloride salts (e.g., NaCl, KCl, RbCl, CsCl, $MgCl_2$, $CaCl_2$, $SrCl_2$, $BaCl_2$), potassium salts (e.g., $K_2SO_3$, KHEPES (2-[4-2-hydroxyethyl)piperazin-1-yl]ethanesulfonic acid, potassium salt), $K_2PIPES$ (piperazine-1,4-bis-2-ethanesulfonic acid, potassium salt), $KHCO_3$, $K_2CO_3$, $KC_2H_3O_2$, KBr, KI, $K_3PO_4$, $KH_2PO_4$, $K_2HPO_4$), sodium salts (e.g., $Na_2SO_3$, NaHEPES, $Na_2PIPES$) and calcium salts (e.g., $Ca(C_2H_3O_2)_2$, $Ca(NO_3)_2$).

The hydrogel may be characterized by its swellability and/or conductivity. Gel swelling, $q_t$, is defined as:

$$q_t = \frac{(m_t - m_{dry})}{m_{dry}} \times 100$$

where $m_t$ is mass of the wet gel and $m_{dry}$ is mass of the dry gel. Swelling is driven by anion-anion repulsive forces. The hydrogel swells and absorbs water until equilibrium between osmotic pressure and elastic restoring force is reached. Swelling capacity depends, in part, on salt concentration and the charge screening effect produced by mobile cations ("ionic cross-linking"). As the charge screening effect increases, swelling decreases. Additionally, as polymer-salt interactions increase, swelling decreases. Swelling is typically less when the electrolyte comprises a divalent cation than when the electrolyte comprises a monovalent cation. As the size of the divalent or monovalent cations increases, $q_t$, increases. Thus, the following swelling trends are observed: $Na^+ < K^+ < Rb^+ < Cs^+$, and $Mg^{2+} < Ca^{2+} < Sr^{2+} < Ba^{2+}$. For example, a hydrogel comprising CsCl typically will swell more than a hydrogel comprising NaCl. In some embodiments, $q_t$, ≤1000%, such as 600-1000%, 600-800%, or 600-700%. Typical ranges are 600-800% for divalent chloride salts, 800-1000% for monovalent chloride salts, 600-700% for KHEPES and $K_2PIPES$, and 800-1000% for other potassium salts.

Desirably the hydrogel, after soaking in electrolyte, has a gel conductivity ≥0.05 S/cm². In some embodiments, the conductivity is 0.07-0.10 S/cm². Conductivity generally increases as cation size increases and/or as polymer-salt interactions decrease. Typical conductivity ranges are 0.06-0.075 S/cm² for NaCl and $MgCl_2$; 0.08-0.10 S/cm² for rest of the chloride salts; 0.05-0.10 S/cm² for most other potassium salts, except for KHEPES, which is about 0.035 S/cm². Other lower conductivity salts (below 0.05 S/cm²) include $Na_2PIPES$ and calcium acetates. The 0.5 M salts (KCl, $KHCO_3$, $KH_2PO_4$, $K_2PIPES$) typically provide a conductivity between 0.035 and 0.055 S/cm².

Advantageously, the hydrogel has minimal swelling and maximum conductivity (FIG. 1). In some embodiments, desirable conditions are obtained when the electrolyte is $CaCl_2$.

IV. Method of Making Hydrogels

Embodiments of the disclosed hydrogels are prepared by combining 2-acrylamido-2-methylpropanesulfonic acid, poly(acrylic acid), a cross-linker and, optionally, a humectant in an aqueous solution. In some embodiments, the AMPS and PAA solutions comprise sodium salts of AMPS and PAA, respectively. Polymerization initiators are added to the solution with mixing. After thorough mixing, the solution is transferred into casting molds and allowed to polymerize for a suitable period of time, e.g., 0.5-30 minutes at room temperature. The polymerization time depends, in part, on the temperature, the initiator composition and/or the initiator concentration. With iron (II) sulfate, polymerization occurs substantially immediately, such as within 30 seconds. With potassium persulfate and potassium metabisulfite, polymerization begins in 5-25 minutes depending on the initiator concentration. In certain examples, polymerization with potassium persulfate and potassium metabisulfite began within 6 minutes (0.15 wt %), 12 minutes (0.1 wt %), or 22 minutes (0.076 wt %). In some embodiments, the hydrogels were left in the molds for several hours to ensure complete polymerization.

The polymerized hydrogels then are soaked in an ionic electrolyte solution comprising mobile ions to remove any unreacted components. Suitable electrolytes include salt solutions. Exemplary salt solutions include, but are not limited to, chloride salts (e.g., 1 M NaCl, KCl, RbCl, CsCl, $MgCl_2$, $CaCl_2$, $SrCl_2$, $BaCl_2$), potassium salts (e.g., 1 M $K_2SO_3$, KHEPES (4-(2-hydroxyethyl)-1-piperazineethanesulfonic acid, potassium salt), $K_2PIPES$ (piperazine-1,4-bis-2-ethanesulfonic acid, potassium salt), $KHCO_3$, $K_2CO_3$, $KC_2H_3O_2$, KBr, KI, $K_3PO_4$, $KH_2PO_4$, $K_2HPO_4$), sodium salts (1 M $Na_2SO_3$, NaHEPES, $Na_2PIPES$) and calcium salts (e.g., 1 M $Ca(C_2H_3O_2)_2$, $Ca(NO_3)_2$). In some embodiments, the electrolyte is a 0.5 M salt solution, e.g., 0.5 M $CaCl_2$, KCl, $KHCO_3$, $KH_2PO_4$, $K_2PIPES$. In certain embodiments, the electrolyte is 1 M $CaCl_2$, 0.5-1 M KCl, 0.5-1 M $KHCO_3$, 0.5-1 M $KH_2PO_4$, or 0.5-1 M $K_2PIPES$. In some embodiments, the electrolyte is a 0.5 M salt solution, e.g., 0.5 M $CaCl_2$, KCl, $KHCO_3$, $KH_2PO_4$, $K_2PIPES$. In certain embodiments, the electrolyte is 1 M $CaCl_2$, 0.5-1 M KCl, 0.5-1 M $KHCO_3$, 0.5-1 M $KH_2PO_4$, or 0.5-1 M $K_2PIPES$.

To maximize conductivity, the hydrogels may be soaked in fresh electrolyte solution for several hours to several days. Prepared hydrogels may be stored between plastic sheets to prevent them from drying out. If a hydrogel has dried out, it can be regenerated by soaking again in an electrolyte solution.

V. Electrodes and Applications

Electrodes comprising an embodiment of the disclosed hydrogels can be used in conjunction with electrochemical impedance spectroscopy (EIS) to characterize the permeability of coatings and detect changes over time. In some embodiments, the coating is a protective coating, i.e., a polymer- or wax-based coating. In other embodiments, the coating is a corrosion and/or flash-rust inhibitor coating. Corrosion/flash-rust inhibitor coatings generally comprise small, water-soluble compounds including, but not limited to, certain amines, phosphate salts (e.g., zinc phosphate), phosphonoxy esters, sodium nitrite, sulfite salts, ascorbic acid, and benzotriazole.

Figure 2:
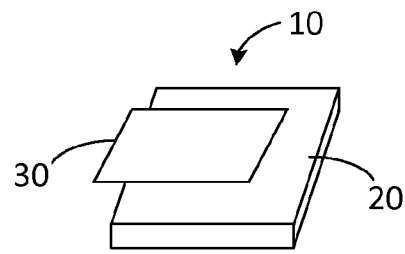
FIG. 2 is a schematic diagram of an exemplary hydrogel electrode.

The electrodes 10 comprise a hydrogel 20 as disclosed herein and an electrical contact 30 in contact with the hydrogel 20 (FIG. 2). The hydrogel is cast, or cut, to a desired size, e.g., 1 cm×1 cm, and placed onto a coating surface. When the hydrogel is applied to a planar surface, it may be laid directly onto the coating. As desired, e.g., when the coating surface is not planar, the hydrogel may be secured in place by any suitable means. In some embodiments, flexible polydimethylsiloxane spacers are used to secure the gel position and maintain a constant gel thickness. An electrical contact is placed onto the hydrogel to provide contact between the hydrogel electrode and a potentiostat. Suitable electrical contacts include metal foils and metal meshes. In some embodiments, the metal is a noble metal (a metal that is corrosion and oxidation resistant in moist air) (e.g., silver, gold, platinum, palladium, ruthenium, rhodium, osmium, iridium) or nickel. In certain embodiments, the metal is silver, gold, nickel, or platinum.

The disclosed hydrogel electrodes are useful for determining whether a coating is impermeable to ions by determining the ability of an electrical current to flow through a coating. Any coating may be evaluated. Coatings may be evaluated (1) when freshly applied to ensure they are continuous and have acceptable barrier properties, and/or (2) periodically over time to ensure that the weathered coating remains protective. Because embodiments of the disclosed electrodes are small and flexible, they are especially suitable for evaluating coatings on a surface that is not flat. Additionally, because the disclosed hydrogel electrodes are non-invasive and non-destructive, they are compatible with art objects, such as sculptures. Embodiments of the disclosed hydrogel electrodes also can be used in situ. Thus, embodiments of the disclosed hydrogel electrodes are useful for evaluating protective and/or corrosion inhibitor coatings on outdoor structures including, but not limited to, sculptures and architectural elements (e.g., railings, poles, gates, bridges, etc.). The underlying substrate may be conductive (e.g., a metal) or non-conductive (e.g., concrete, plaster).

Traditional measurement methods are performed using a standard fluid electrochemical cell with a counter electrode placed on a coated surface and a working electrode in contact with the underside of the underlying substrate (or the underside of the substrate itself may be the working electrode). A current is applied and flows through both the substrate and the coating. The standard fluid cell is useful only when the substrate is conductive and an area of bare substrate is accessible for attachment of the working electrode.

In one embodiment, a gel electrode is placed on the surface of a coated, electrically conductive substrate. The underside of the substrate functions as the second electrode. A small alternating current is applied. The current may be 5-40 mV$_{rms}$, such as 10-30 mV$_{rms}$ or 15-25 mV$_{rms}$. In certain examples, the current was 20 mV$_{rms}$. The current flows through coating to the underside of the substrate (or an electrode in contact therewith). The current flow between the two electrodes is indicative of how well the coating is performing.

In some embodiments, two gel electrodes are placed directly on the surface of a coated object. The two electrodes are laterally spaced apart. In certain examples, two gel electrodes, each having an area of 1 cm$^2$, were placed 1 cm apart (edge-to-edge). The two electrodes and the surface coating form an electrochemical cell. A small alternating current is applied. The current may be 5-40 mV$_{rms}$, such as 10-30 mV$_{rms}$ or 15-25 mV$_{rms}$. In certain examples, the current was 20 mV$_{rms}$. The current takes the path of least resistance between the two electrodes. In some embodiments, the current flows from the first electrode through the coating to the second electrode without passing through the substrate. Advantageously, this arrangement eliminates any need for electrical contact to the underlying substrate itself and allows coating performance to be measured on a non-conductive or conductive substrate. In another embodiment, when the substrate is conductive, the current may flow from the first electrode down through the coating into the substrate, through the substrate, and back up through the coating to the second electrode; this current path typically indicates that the coating has become porous and may not be protective. The current flow between the two electrodes is indicative of how well the coating is performing.

In some examples, a reference electrode also is used. The reference electrode may be a hydrogel electrode as disclosed herein. In such embodiments, a reference direct current voltage is applied between the reference and working electrodes, while a variable alternating current is applied between the counter and working electrodes.

While relatively easy to produce, EIS data requires detailed interpretation often involving circuit modeling to give sufficient insight into the spectral changes observed. While full circuit modeling of the data described here is not shown, numerous publications demonstrate the utility of fitting data sets to constructed circuit models that represent the physical system being monitored (Swartz and Clare, *Electrochimica Acta* 62, 199-206, 2012, the relevant teachings of which are incorporated herein by reference; Swartz, et al., *Progress in Organic Coatings* 75, 3:215-223, 2012, the relevant teachines of which are incorporated herein by reference, Cano, et al., *Journal of Solid State Electrochemistry* 14, 3:453-463, 2010).

Electrochemical impedance measured by applying an AC potential to an electrochemical cell and then measuring the current through the cell. Electrochemical impedance is typically measured using a small excitation signal, e.g., a small AC perturbation, such as a perturbation of 20 mV. In a linear or pseudolinear system, the current response to a sinusoidal potential is a sinusoid at the same frequency, but shifted in phase. The excitation signal, expressed as a function of time has the form:

$$E_t = E_0 \sin(\omega t)$$

where $E_t$ is the potential at time t, $E_0$ is the amplitude of the signal, and $\omega$ is the radial frequency. The relationship between radial frequency $\omega$ (radians/second) and frequency f (hertz) is:

$$\omega = 2\pi f$$

In a linear system, the response signal, $I_t$, is shifted in phase ($\theta$) and has a different amplitude than $I_0$.

$$I_t = I_0 \sin(\omega t + \theta)$$

An expression analogous to Ohm's Law calculates the impedance of the system as:

$$Z = \frac{E_t}{I_t} = \frac{E_o}{I_o} \frac{\sin(\omega t)}{\sin(\omega t + \theta)} = Z_o \frac{\sin(\omega t)}{\sin(\omega t + \theta)}$$

Thus, the impedance is expressed in terms of magnitude, $Z_0$, and phase shift, $\theta$. For a resistor, $Z_R = R$ (where R=resistance)

when θ=0°. For a capacitor, $Z_C=1/j\omega C$ (where C=capacitance, and j=square root of −1) when θ=90° with respect to voltage. For an inductor, $Z_L=1/j\omega L$ when θ=−90° with respect to voltage.

Capacitors in EIS studies may act like a constant phase element (CPE). The impedance of the capacitor can be expressed as:

$$Z_{CPE}=1/Y_0(j\omega)^\alpha$$

where $Y_0$ is the capacitance, and α is an exponent equaling 1 for a capacitor. For a CPE, the exponent α is less than 1.

In a simple interpretation of EIS data, decreased total impedance in a low frequency range (less than 1 Hz) is associated with coating permeability/failure. While films with an impedance, |Z|, greater than 1 MΩ are considered protective, deviations from linearity at low frequencies suggest a coating is somewhat permeable to the passage of ions even though its total impedance may still exceed 1 MΩ (Kosec, et al., *Progress in Organic Coatings* 2010, 69(2): 199-206). The time constant, which is the inverse of the frequency when the phase angle, θ, is equal to −45°, can be used as a measure of the permeability of the film (the smaller, faster time constant, the poorer the film's barrier properties). In some embodiments, a time constant less than 75 milliseconds (based on a coating capacitance of 1.0 nF) indicates a coating that is protective against corrosion.

The gel electrodes have low impedance (less than 10 kΩ at 0.1 Hz), so as to not interfere with EIS measurements, and they are cleanly removable and non-damaging to the coating or underlying substrate. Both the working and counter electrodes are surface-mounted, thereby circumventing the requirement of existing technology to make direct electrical contact with the substrate. Because the hydrogels' impedance demonstrate behavior that can be fit using electrical elements from simple circuits, the hydrogels' impedance response can be subtracted from the system when measuring the impedance of the a coating. In other words, a background subtraction can be done to remove the hydrogels' impedance so that only the coating's impedance is measured.

When using embodiments of the disclosed surface-mounted electrochemical cells, the current follows the path of lowest impedance, which may direct it through shallower surface layers of the coating, rather than penetrating the bulk of the coating. This distinction between surface-mounted and traditional electrochemical cells may provide further insight into the weathering of coatings as a top down process or a homogeneous degradation process (as spectral differences between the two geometries suggest that different current paths are taken). A comparison of EIS data for the two different geometries demonstrates that spectral differences are especially evident by careful inspection of the phase angle versus frequency plot in the surface-mounted EIS geometry. Advantageously, the small size of the hydrogel electrodes enables better detection of coating defects compared to traditional electrochemical cells. Defects were more apparent in the gel measurements. For example, in area 1 of FIGS. 4A-B and area 2 of FIGS. 5A-B, lower impedances were observed in the slower frequency range.

VI. Kits

Embodiments of a kit for performing electrochemical evaluation of coatings include a hydrogel or a hydrogel electrode comprising a cross-linked poly(acrylic acid-co-2-acrylamido-2-methyl-1-propanesulfonic acid) hydrogel as disclosed herein. In some embodiments, the kit includes a plurality of hydrogel electrodes. The kit also may include an electrolyte solution. In certain embodiments, the kit includes one or more spacers (e.g., polydimethylsiloxane spacers) that can be used to secure the gel to a coated surface, such as a non-planar surface.

VII. Examples

Materials & Methods

Coated Substrates for Laboratory Studies.

Bronze substrates (2.54×7.62 cm; 90% Cu 10% Sn, TB Hagstoz & Son Inc.) were coated with Paraloid® B-44 resin (The Dow Chemical Company), principally composed of poly(methyl methacrylate-co-ethyl acrylate) using a Fuji HVLP Super 4 XPC™ spray system (Fuji Industrial Spray Equipment Ltd, Toronto, ON) for a dry film thickness of approximately 12 μm for each of two layers and for a total dry film thickness of approximately 25 μm. Thickness measurements were acquired as an average of ten trials with a PosiTector 6000 coating thickness gage (DeFelsko Corporation, Ogdensburg, N.Y.). Coated substrates were mechanically poked with a diamond scribe or weathered in Portland, Oreg. USA for 32 months at the time of measurements.

Hydrogel Synthesis.

All chemicals were obtained from Sigma-Aldrich. The sodium salts of 2-acrylamido-2-methylpropanesulfonic acid (AMPS; 50 wt % solution in water) and poly(acrylic acid) (PAA; average MW ~5100) along with the cross-linker N,N'-methylenebis(acrylamide) (MBA; 1 wt % solution) were polymerized via the potassium persulfate (KPS) and metabisulfite (KMBS) redox initiator system (1 wt % solutions). Glycerol was included as a humectant. The monomer solution was prepared by mixing the glycerol with the AMPS, PAA, and MBA solutions together, stirring thoroughly, and then purging briefly with nitrogen gas. Each initiator was added at 0.12 wt % of AMPS, and the solution was stirred again for 5 minutes to ensure even distribution before being transferred into casting molds (two 10 cm×10 cm glass plates with a 1 mm thick bonded spacer). The hydrogel sheets polymerized at room temperature within 15 minutes, but were left in the molds overnight to ensure complete polymerization. In weight percent, the final composition of the hydrogel was 18.59% AMPS, 11.21% PAA, 0.27% MBA, 11.27% glycerol, 0.02% each KPS and KMBS, and 58.61% water. After soaking for a day in 1 M $CaCl_2$ to rinse and remove any unreacted components, the hydrogel sheets were moved into a fresh $CaCl_2$ solution and left to equilibrate for several days to maximize conductivity. The gels were then removed from solution and stored between plastic sheets until needed for EIS measurements.

Electrochemical Impedance Spectroscopy.

Figure 3:
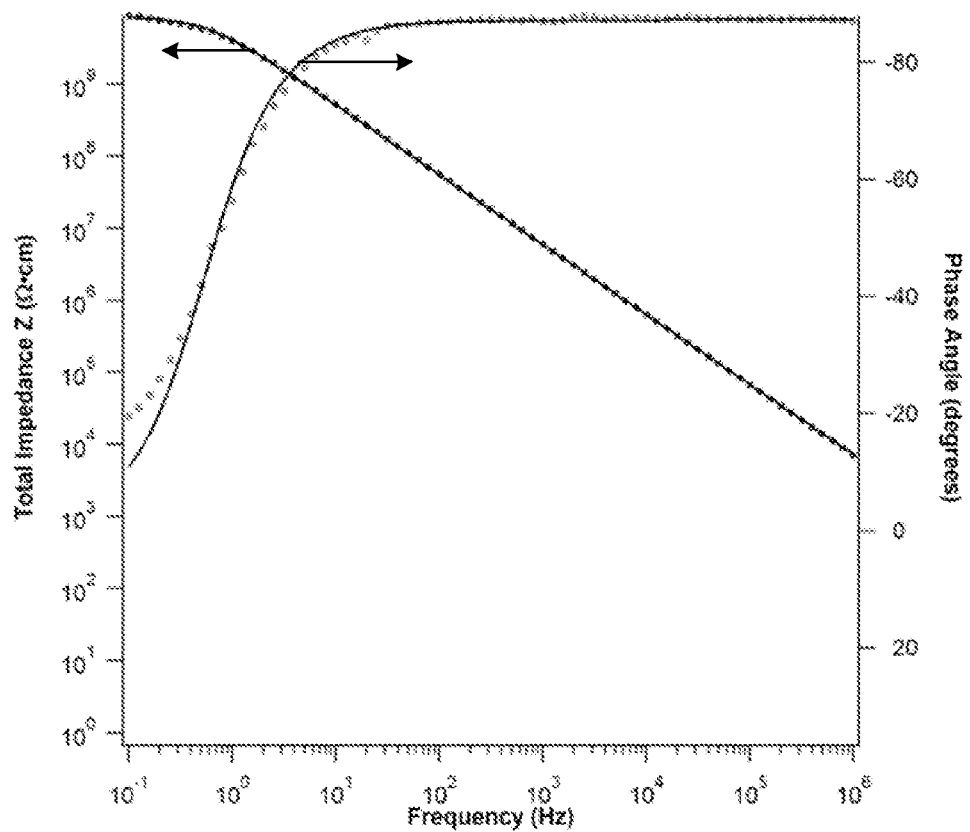
FIG. 3 is an exemplary electrochemical impedance spectrum.

Gel electrodes were cut to approximately 1 cm×1 cm each and placed on the coating surface with flexible PDMS spacers (polydimethylsiloxane, Dow Corning, Sylgard® 184, 1 mm thick) to secure the gel position and maintain a constant gel thickness. Silver foil strips (0.1 mm thick, Premion for Alfa Aesar) were placed on the top of the gel electrodes to provide the electrical contact with the potentiostat (Gamry REF600, Gamry Instruments, Warminster, Pa.). EIS spectra were recorded from 1 MHz to 0.1 Hz with an applied AC voltage of 20 $mV_{rms}$ versus the open circuit potential. An exemplary electrochemical impedance spectrum is shown in FIG. 3. Standard fluid paint test cells were obtained from Gamry Instruments and filled with 1 M $CaCl_2$. Gel measurements were taken after standard cell measurements to ensure coating permeability. The poked coating was soaked for 28 hours in 1 M $CaCl_2$ before standard cell and gel measurements. The outdoor weathered coating was soaked for 4 hours before measurements. All EIS spectra were normalized to the area component of the cell constant in order to account for differences in electrode area between the standard cell and the hydrogels, and also between the one and two cell configurations. The normalization factor is $$K_{cell,area} = \frac{1}{A_1} + \frac{1}{A_2} \quad (1)$$

where $A_1$ is the electrode area for a single cell measurement, and $A_2$ is the area of the second electrode if using a two cell EIS configuration. The standard fluid cell area was 14.62 $cm^2$ and each hydrogel area was measured precisely with calipers.

Results:

EIS measurements of coatings of Paraloid® B-44 on bronze substrates were taken using both standard fluid cells and hydrogel electrodes. To observe the sensitivity of the measurement, spectra from two different areas were taken using the reverse side of the substrate as the working electrode and either one fluid cell with a graphite rod or a hydrogel with silver foil as the counter electrode. In these arrangements, the applied current flowed between the working and counter electrode, passing vertically through the coating. After accounting for conducting area and cell constants, the normalized spectra showed similarities in both |Z| versus frequency and phase versus frequency, and indicated that surface-mounted hydrogels could be used to obtain comparable data to standard fluid cells (England et al., *Electroanalysis* 2014, 26:1059-1067).

Figure 4A:
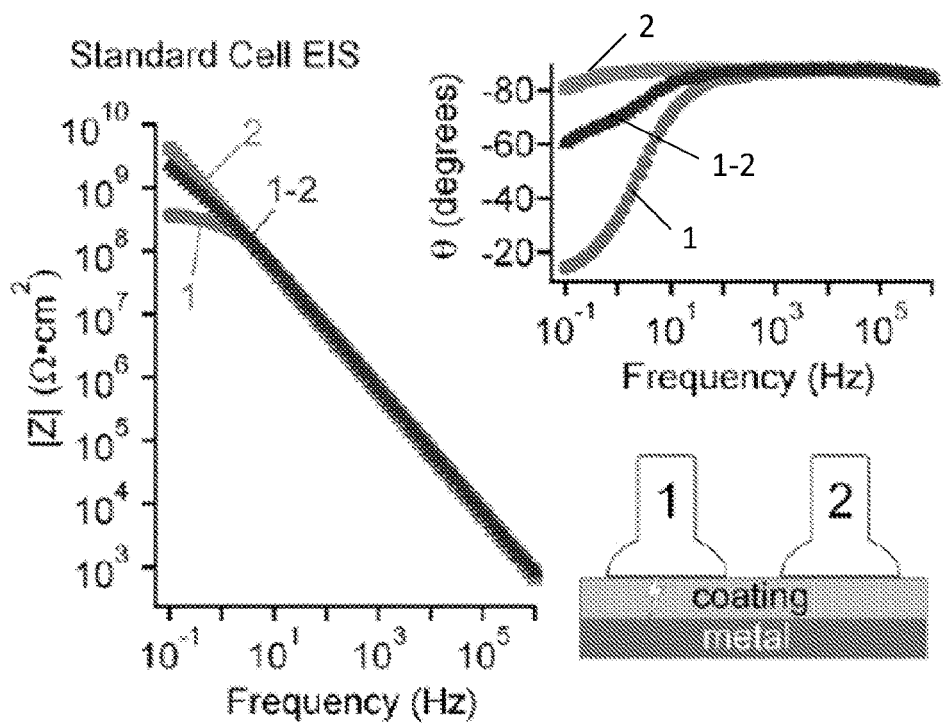
FIGS. 4A and 4B are a comparison of single cell and double cell EIS measurement for standard fluid cells (4A) and surface-mounted hydrogels (4B). Area #1 was 16.1±1.5 µm thick; area #2 was 21.3±3.7 µm thick. For the traces labeled 1 or 2, the substrate was the working electrode, and either area #1 or area #2 was the counter electrode. For the traces labeled 1-2, one area was the counter electrode and the other was the working electrode.
Figure 4B:
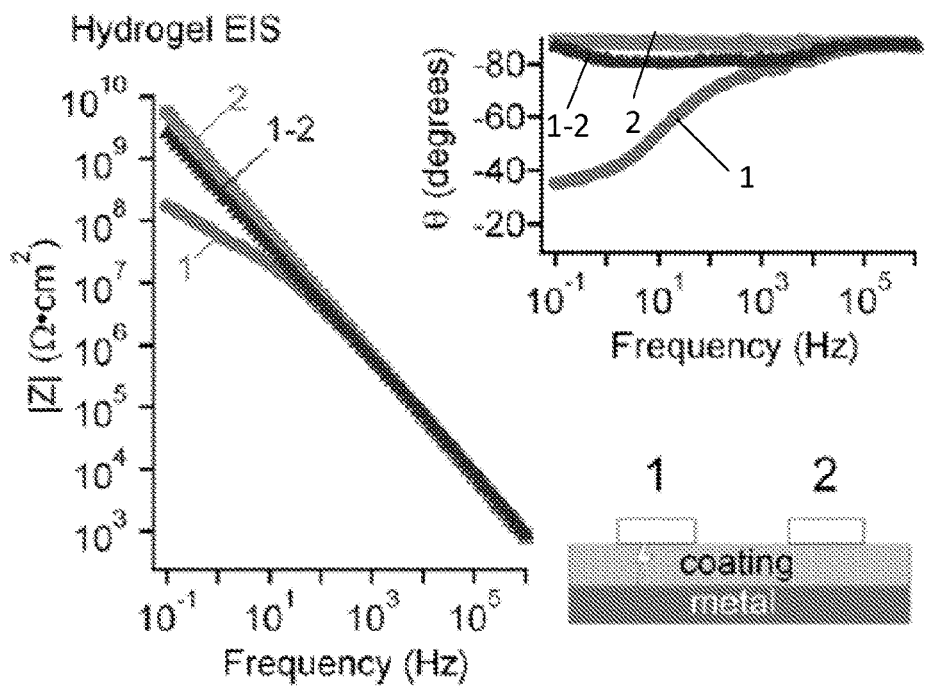

Although visually both areas selected for EIS measurements appeared identical, a cursory inspection of the EIS data in FIGS. 4A-4B shows that the two data sets diverged in the lower frequency range: area 1 had a total impedance of 370 MΩ at 0.1 Hz for the standard cell and 176 MΩ for the hydrogel and area 2's impedance was 4.2 GΩ at 0.1 Hz for the standard cell and 5.6 GΩ for the gel. The total impedance of area 1 at 0.1 Hz exceeded 1 MΩ and as such is considered "protective". However, because the data deviated from linearity in the monitored region, the film likely contained a small defect, allowing the passage of ions and a small amount of activity to occur at the metal surface. Such a defect was not observed in area 2 as the total impedance remained high and the phase angle remained close to -90° at all frequencies measured, suggesting mostly capacitive behavior under all frequencies measured. In the case of the standard cell at area 1, the time constant was 0.500 s as compared to 0.399 s for the hydrogel and confirmed that both cell geometries were able to differentiate between ideal and nearly ideal portions of the protective coating.

While the data taken from areas 1 and 2 suggested that EIS, configured using either fluid or hydrogel cells, is sensitive to small defects within films, making electrical contact to an uncoated portion of the substrate is oftentimes neither feasible nor acceptable. Usually, for works exposed outdoors there is no surface left uncoated and it is for those applications that surface-mounted electrodes are particularly useful. For these measurements, one piece of hydrogel served as the counter electrode and a second hydrogel, laterally displaced from the first, served as the working electrode (FIG. 4B). This surface-mounted arrangement eliminated the need for electrical contact to the substrate itself. To permit comparison with the gels, two laterally separated fluid cells were assembled as shown in the schematic in FIG. 4A. In the surface-mounted geometry, the applied current flowed from one cell to the other via the path of lowest impedance, which can deviate from the actual footprint of the cells (Qi et al., *Corrosion* 2010, 66(2), article 025002; Qi et al., *Corrosion* 2009, 65(5):343-349). After normalizing for the area as shown in equation 1, the data labeled 1-2 in FIGS. 4A-4B was obtained. Laterally displaced electrodes produced data that appeared to be an intermediary, though not exactly an average, of area 1 and area 2.

To further understand the EIS spectral features associated with damaged coatings, films of Paraloid® B-44 on bronze substrates were intentionally damaged by poking a single small hole (diameter of 27 μm) through the film (FIGS. 5A-5B) and weathered naturally outdoors in Portland, Oreg. USA for 32 months (FIGS. 6A-6B). Producing a hole in the film exposed the substrate to corrosive ions, which formed a corrosion layer during a period of 28 h. After ensuring that EIS traces taken at least one hour apart overlapped, spectra were taken using standard fluid cells in areas 1 and 2 before and after the holes were made, with the acquired data shown in FIGS. 5A-5B. The magnitude of the impedance at lower frequencies was clearly depressed (showing values of $10^6$-$10^8$ $\Omega cm^2$ at 0.1 Hz in FIGS. 5A-5B) when compared with a nearly intact film (with values exceeding $10^8$ $\Omega cm^2$ at 0.1 Hz as is shown in FIGS. 4A-4B).

The trace labeled "1, before" in FIG. 6A was the EIS spectrum of the coated panel in area 1 before it was weathered outdoors; the high impedance in the lower frequency range and the broad -90° phase angle plateau are features of a nearly ideal coating. After weathering, the traces labeled 1 and 2 showed decreases in the magnitude of the impedance at frequencies less than $10^3$ Hz as well as faster time constants. The data showed that damage such as a hole or weathering of a coating was detectable by EIS as a reduction in the impedance at lower frequencies and that damage may also be detected using hydrogel cells. It should be noted that corrosion formed on the substrate only in small specks, likely where small defects formed during weathering. While the visual appearance of the substrate remained good, changes in the permeability of the film after weathering for 32 months were clearly observed by EIS spectral changes; thus EIS has been demonstrated to be a highly sensitive tool for the detection of nearly invisible damage to coatings.

Figure 5A:
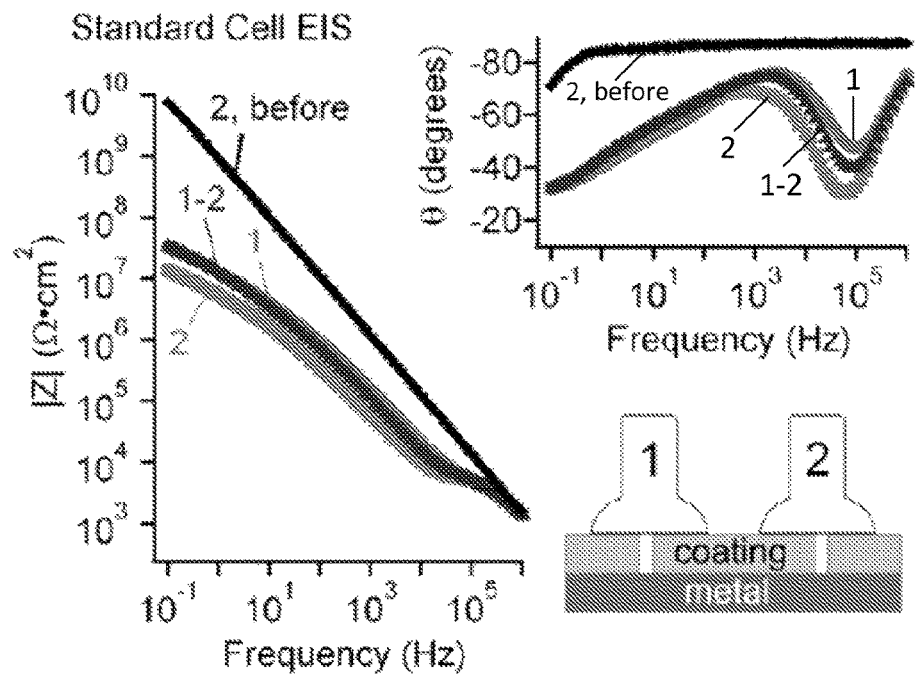
FIGS. 5A and 5B are a comparison of single cell and double cell EIS measurement for both standard fluid (5A) and hydrogel (5B) cells on a Paraloid® B-44-coated bronze with intentionally damaged coating. One hole was made in each area using a diamond scribe. Area #1 was 27.5±0.8 µm thick; area #2 was 32.6±2.2 µm thick.
Figure 5B:
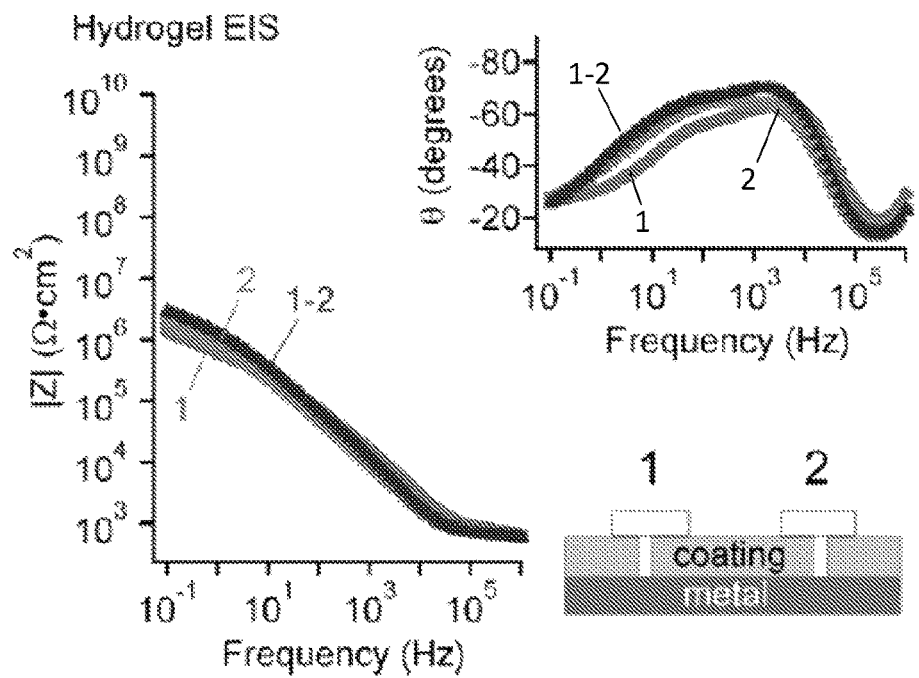
Figure 6A:
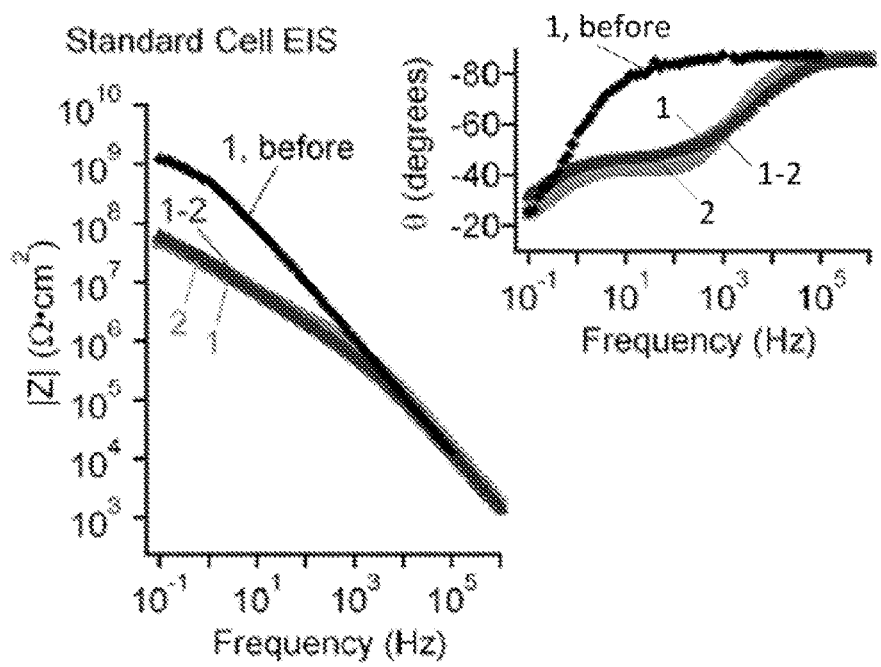
FIGS. 6A and 6B show results for a Paraloid® B-44-coated bronze panel weathered outdoors for 32 months. A comparison using standard fluid cells (5A) and hydrogel cells (5B) was performed. Area #1 was 24.1±1 µm thick; area #2 was 34.5±2.1 µm thick.
Figure 6B:
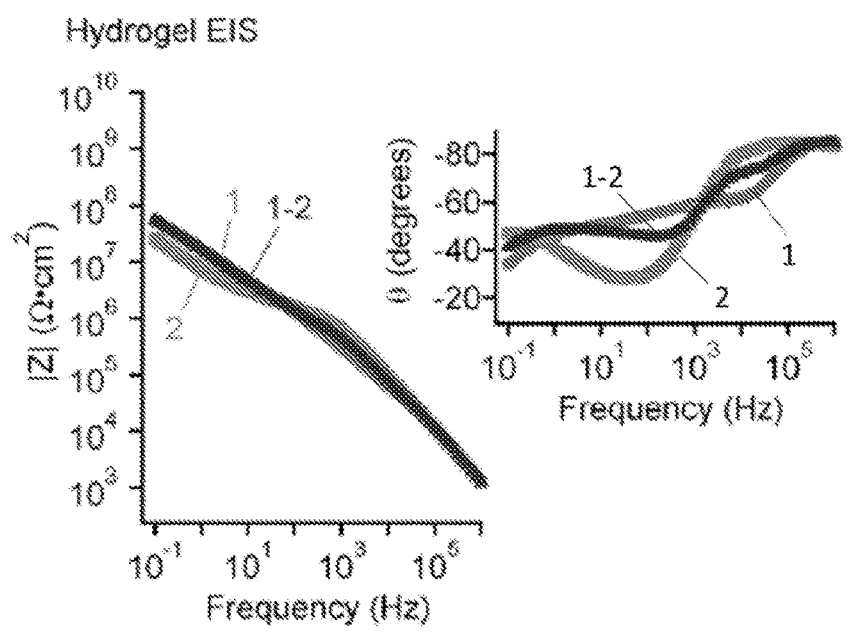
Figure 6C:
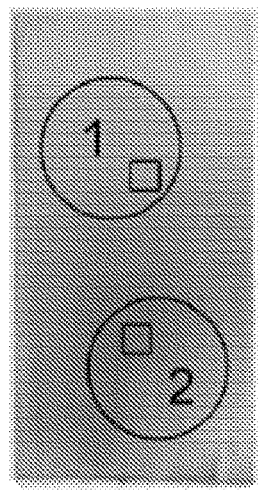
FIG. 6C is a photograph showing the areas measured by the standard cells (circles) and gel electrodes (squares) of FIGS. 5A, 5B, 6A and 6B.

Interestingly, the effect of a defect in the intentionally damaged panel was more apparent in the EIS spectrum collected using hydrogel cells in FIG. 5B, compared to the fluid cells in FIG. 5A. The magnitude of the impedances for the hydrogels was lower (showing values between $10^6$-$10^7$ $\Omega cm^2$ at 0.1 Hz in FIG. 5B and $10^7$-$10^8$ $\Omega cm^2$ at 0.1 Hz in FIG. 5A.) This discrepancy was likely an effect of the difference in electrode area. The ratio of the area of the hole to cell was different for the two cell types: the electrode area for each hydrogel was 1.00 $cm^2$ (FIG. 6C, squares), while that for the fluid cell was 14.62 $cm^2$ (FIG. 6C, circles), which resulted in lower total impedances as measured by hydrogel cells compared to standard cells. This result indicates that smaller electrode footprints may more accurately pinpoint damaged areas and also enable spatially distributed measurements of finer resolution.

To simulate the common scenario where electrical contact cannot be made to a substrate, two laterally displaced cells were used, labeled 1-2 in FIGS. 5A-5B and 6A-6B. Comparing that data to the single cell data gave insight into the sensitivity of the surface-mounted method. Because the surface-mounted method encompassed twice the area, small defects that dominated a single cell measurement were less apparent, but still detectable in the surface-mounted, double cell measurements. The fact that the presence of defects was still detectable in the surface-mounted method indicates that this geometry is indeed compatible with onsite measurements.

Figure 7:
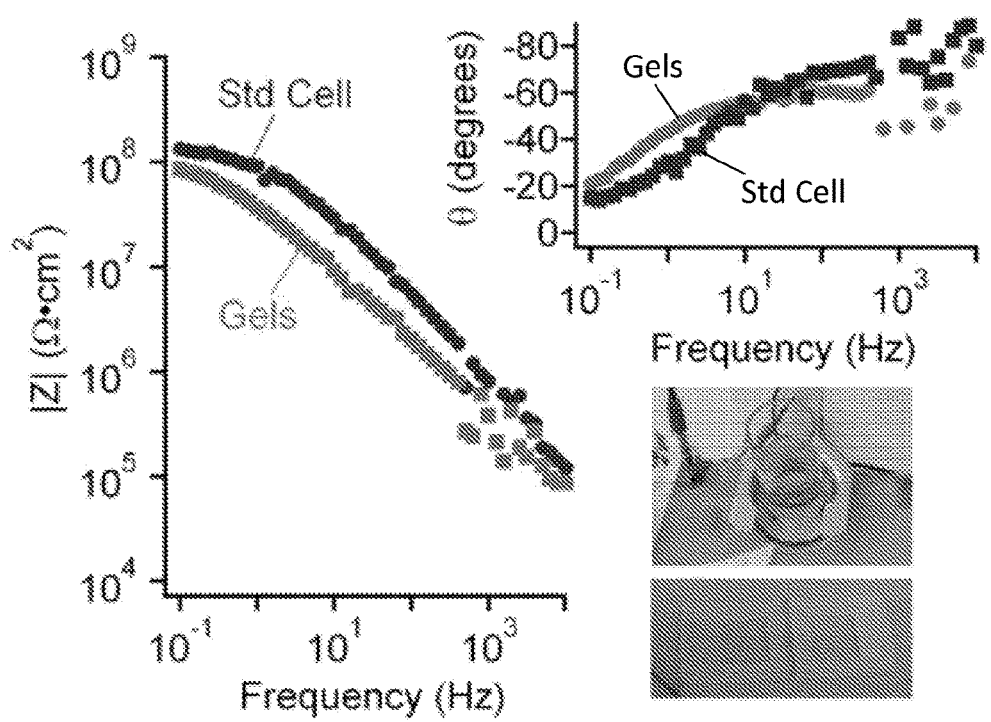
FIG. 7 shows results for a coated sculpture. A comparison was performed using gels and standard cells by EIS for standard fluid cells and surface-mounted hydrogel cells on the primer coat (approximately 150 µm thick) of a hatch door of the sculpture. Inset photographs show the standard cell (top panel) and the position of the gels in the same area (lower panel; only the PDMS spacers are shown).

Therefore as a test in the utility of EIS as an onsite monitoring tool, both a single fluid cell (with the substrate as the working electrode) and two surface-mounted, laterally separated hydrogel cells were applied to a door hatch of Tony Smith's sculpture, The Stinger, at Olympic Sculpture Park (Seattle, Wash.) and EIS measurements made. FIG. 7 shows the resulting spectra produced from the standard fluid cell and hydrogel cells. The overall trend and shape in both the impedance and phase angle versus frequency was similar, though some differences in magnitude and phase were observable. The differences were likely due to the fact that the fluid cell geometry included the oxide layer of the substrate, while the geometry of the surface-mounted hydrogel electrodes did not and thus exhibited lower total impedance. The data showed that the primer coat is slightly permeable to ions, comparable to the Paraloid® B-44 coated panel in FIGS. 6A-6B. This experiment demonstrated that EIS can be used as an onsite measurement tool. The measurements made onsite showed considerable noise in the data between $10^3$ and $10^4$ Hz, though the cause was unknown. However, key frequencies associated with coating permeability are lower than this band of noise.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An electrode, comprising:
a cross-linked poly(acrylic acid-co-2-acrylamido-2-methyl-1-propanesulfonic acid (poly(AA-AMPS)) hydrogel comprising 17-25 wt % 2-acrylamido-2-methyl-1-propanesulfonic acid (AMPS), 10-20 wt % poly(acrylic acid), a cross-linker in an amount equal to 1-2 wt % of the mass of AMPS, and 50-65 wt % water; and
an electrical contact in contact with the hydrogel.

2. The electrode of claim 1, wherein the cross-linker is N,N'-methylenebis(acrylamide).

3. The electrode of claim 1, wherein the cross-linked poly(AA-AMPS) hydrogel further comprises a humectant.

4. The electrode of claim 3, wherein the humectant is glycerol, and the cross-linked poly(AA-AMPS) hydrogel comprises 7-18 wt % glycerol.

5. The electrode of claim 1, further comprising an ionic electrolyte incorporated into the hydrogel.

6. The electrode of claim 5, wherein the ionic electrolyte comprises NaCl, KCl, RbCl, CsCl, $MgCl_2$, $CaCl_2$, $SrCl_2$, $BaCl_2$, $K_2SO_4$, 2-[4-(2-hydroxyethyl)piperazin-1-yl]ethanesulfonic acid potassium salt, piperazine-1,4-bis-2-ethanesulfonic acid potassium salt, $KHCO_3$, $K_2CO_3$, $KC_2H_3O_2$, KBr, KI, $K_3PO_4$, $KH_2PO_4$, $K_2HPO_4$), $Na_2SO_3$, 2-[4-(2-hydroxyethyl)piperazin-1-yl]ethanesulfonic acid sodium salt, piperazine-1,4-bis-2-ethanesulfonic acid sodium salt, $Ca(C_2H_3O_2)_2$, $Ca(NO_3)_2$, or a combination thereof.

7. The electrode of claim 1, wherein the cross-linked hydrogel has a maximum gel swelling, $q_r$, ≤1000%.

8. The electrode of claim 1, wherein the electrical contact is a metal foil or mesh.

9. The electrode of claim 8, wherein the metal foil or mesh is a silver, gold, nickel, or platinum foil or mesh.

10. A method for evaluating permeability of a coating on a substrate, comprising:
placing a first electrode in contact with the coating, the first electrode comprising (i) cross-linked poly(acrylic acid-co-2-acrylamido-2-methyl-1-propanesulfonic acid (poly(AA-AMPS)) hydrogel comprising 17-25 wt % 2-acrylamido-2-methyl-1-propanesulfonic acid (AMPS), 10-20 wt % poly(acrylic acid), a cross-linker in an amount equal to 1-2 wt % of the mass of AMPS, 50-65 wt % water, a humectant, and an ionic electrolyte, and (ii) an electrical contact in contact with the hydrogel;
placing a second electrode in contact with the coating and laterally spaced apart from the first electrode, the second electrode comprising (i) cross-linked (poly(AA-AMPS)) hydrogel comprising 17-25 wt % AMPS, 10-20 wt % poly(acrylic acid), and a cross-linker in an amount equal to 1-2 wt % of the mass of AMPS and (ii) an electrical contact in contact with the hydrogel;
applying an alternating current between the first electrode and the second electrode;
recording an electrochemical impedance spectrum; and
evaluating the electrochemical impedance spectrum to determine whether the coating is permeable to ions.

11. The method of claim 10, wherein the first electrode and the second electrode have the same chemical composition.

12. The method of claim 10, wherein the substrate is not electrically conductive.

13. The method of claim 10, wherein the alternating current is 5-40 $mV_{rms}$.

14. The method of claim 10, wherein the coating is a polymer- or wax-based coating, and a total impedance >1 MΩ in a frequency range less than 1 Hz indicates the coating is non-permeable to ions.

15. The method of claim 10, wherein the coating is a corrosion inhibitor coating, and a total impedance >10 kΩ in a frequency range less than 1 Hz indicates the coating is non-permeable to ions.

16. The method of claim 10, wherein the electrochemical impedance spectrum is measured over a range from 0.1 Hz to 1,000 Hz, the method further comprising determining whether the electrochemical impedance spectrum deviates from linearity over a measured frequency range, wherein nonlinearity indicates the coating is permeable to ions.

17. The method of claim 10, further comprising determining a time constant, wherein a time constant of less than 75 milliseconds indicates the coating is non-permeable to ions and wherein the time constant is the inverse of the frequency when the phase angle, θ, is equal to −45° as measured by electrochemical impedance spectroscopy.

18. A method for evaluating permeability of a coating on a surface of an electrically conductive substrate, comprising:
placing a first electrode in contact with the coating, the first electrode comprising (i) cross-linked poly(acrylic acid-co-2-acrylamido-2-methyl-1-propanesulfonic acid (poly(AA-AMPS)) hydrogel comprising 17-25 wt % 2-acrylamido-2-methyl-1-propanesulfonic acid (AMPS), 10-20 wt % poly(acrylic acid), a cross-linker in an amount equal to 1-2 wt % of the mass of AMPS, 50-65 wt % water, a humectant, and an ionic electrolyte, and (ii) an electrical contact in contact with the hydrogel;

applying an alternating current between the first electrode and an opposing surface of the electrically conductive substrate;

recording an electrochemical impedance spectrum; and evaluating the electrochemical impedance spectrum to determine whether the coating is permeable to ions.

* * * * *